United States Patent [19]

Davis

[11] Patent Number: 5,321,180

[45] Date of Patent: Jun. 14, 1994

[54] CONVERSION OF VINYLCYCLOHEXENE TO ETHYLBENZENE

[75] Inventor: Clark S. Davis, Mobile, Ala.

[73] Assignee: Union Carbide Chemicals & Plastics Technology Corporation, Danbury, Conn.

[21] Appl. No.: 57,320

[22] Filed: May 5, 1993

[51] Int. Cl.$^5$ .............................................. C07C 5/367
[52] U.S. Cl. .................................. 585/431; 585/430
[58] Field of Search .............................. 585/430, 431

[56] References Cited

U.S. PATENT DOCUMENTS

| | | | |
|---|---|---|---|
| 2,771,495 | 11/1956 | Pines et al. | 585/431 |
| 3,080,432 | 3/1963 | Voltz et al. | 260/666 |
| 3,278,618 | 10/1966 | Amagasa et al. | 260/666 |
| 3,308,192 | 3/1967 | Bajars | 260/680 |
| 3,329,736 | 7/1967 | Butte et al. | 260/683.2 |
| 3,340,317 | 9/1967 | Kenton | 260/666 |
| 3,347,944 | 10/1967 | Fritz et al. | 260/666 |
| 3,363,015 | 1/1968 | Kittleman | 260/666 |
| 3,390,193 | 6/1968 | Kreider | 260/666 |
| 3,511,885 | 5/1970 | Hughes | 260/666 |
| 3,578,724 | 5/1974 | Hubert | 260/678 |
| 3,855,327 | 12/1974 | Billings | 260/668 |
| 3,903,185 | 9/1975 | Vogel et al. | 260/668 |
| 4,029,715 | 6/1977 | Rieve et al. | 260/668 |
| 4,034,052 | 7/1977 | Puskas | 260/671 |
| 4,048,243 | 9/1977 | Ruckelshauss | 585/431 |
| 4,233,244 | 11/1980 | Patterson et al. | 564/423 |
| 4,239,929 | 12/1980 | Masilamani et al. | 585/442 |
| 4,359,594 | 11/1982 | Patterson et al. | 585/440 |
| 4,409,417 | 10/1983 | Herbstman | 585/660 |

OTHER PUBLICATIONS

Alieva et al., "4-vinyl-1-cyclohexene Conversion in the Presence of Anionic Catalysts", Zh. Khim. Obshchest., 17(5):588-9 (1972).

Ruckelhauss et al., "Isomerizing Dehydrogenation of 4-vinyl Cyclohexene to Ethylbenzene", Chem. Ztg., 101(2):103-5 (1977).

Renger et al., "Cyclodimerization of Butadiene on Copper Silica Catalyst", Z. Chem., 19(5):194-5 (1979).

Primary Examiner—Asok Pal
Assistant Examiner—P. Achutamurthy
Attorney, Agent, or Firm—W. K. Volles

[57] ABSTRACT

Vinylcyclohexene is converted to ethylbenzene by contacting vinylcyclohexene with an alkali metal, liquid ammonia and an initiator. The method of the present invention allows the reaction to be conducted in a single step while selectively producing ethylbenzene with yields exceeding 95 percent by weight 10 Claims, No Drawings

CONVERSION OF VINYLCYCLOHEXENE TO ETHYLBENZENE

FIELD OF THE INVENTION

The present invention relates to the dehydrogenation of cyclic diene compounds. More specifically, the present invention relates to the production of ethylbenzene from vinylcyclohexene.

BACKGROUND OF THE INVENTION

Ethylbenzene is produced on commercial scale by the alkylation of benzene with ethylene. Due to periodic shortages and the hazardous nature of benzene, attempts have been made to produce ethylbenzene by methods other than alkylation of benzene with ethylene.

U.S. Pat. No. 2,745,887 discloses a process for treating with alkali metals cyclic hydrocarbons having 6 carbon atoms in the ring and containing at least two double bonds, at least one of them in the ring. However, this process is not feasible for commercial purposes since induction periods of 12–15 hours occur before the reaction is initiated, unless activators are added such as, for example, o-chlorotoluene, which reduce the induction period to 4–5 hours, or unless the process is carried out in the presence of extremely expensive and dangerous sodium hydride. However, even in these cases, only degrees of conversion of up to 71 percent are attained. Furthermore, it was found that this process does not yield useful results when vinylcyclohexene is used.

Furthermore, it is known from U.S. Pat. No. 3,903,185 that cycloolefins having 8 carbon atoms can be converted over catalysts of Subgroups VI to VIII, including the platinum group, of the Periodic Table of the elements, at temperatures of 350°–450° C., under pressures of 2.5–30 atmospheres absolute and in the presence of 0.2–20 m$^3$ of hydrogen per kilogram of C$_8$-cycloolefin, to obtain ethylbenzene in rather satisfactory yields. However, this process is commercially very expensive, because it must be carried out at high temperatures, under pressure, and in the presence of hydrogen.

U.S. Pat. No. 4,048,243 discloses the dehydrogenation of cycloolefins by passing the cycloolefins over catalysts containing an alkali metal on a aluminum oxide support. The process is conducted at temperatures of about 20°–150° C. and pressure of about 0.8–2 atmospheres. This process requires the manufacture of a heterogeneous supported catalyst in a separate step which requires operation of the catalyst from the product in a later step.

Despite the disclosures of the prior art a need exists for the production of ethylbenzene in a method which produces ethylbenzene in high yields and in a cost-effective manner.

SUMMARY OF THE INVENTION

The present invention provides a method of converting vinylcyclohexene into ethylbenzene and hydrogen by contacting vinylcyclohexene with an alkali metal, an initiator and liquid ammonia.

DETAILED DESCRIPTION OF THE INVENTION

Isomeric cyclohexenes are readily available commercial compounds produced from the dimerization of butadiene, the commercial production of 1,5,9 cyclododecatriene, and the use of the C$_4$ fraction as disclosed in U.S. Pat. No. 3,897,508.

According to the method of the present invention, the vinylcyclohexene is contacted with an alkali metal, an initiator and liquid ammonia for a sufficient time so as to produce an alkali metal amide. Without wishing to be bound by any theory it is believed that the resulting alkali metal amide specie formed acts as the catalytic entity in the ethylbenzene-forming reaction. Suitable alkali metal amides include, but are not limited, to LiNH$_2$, NaNH$_2$, KNH$_2$ and mixtures thereof. In a particularly preferred embodiment of the present invention, the amide catalyst is prepared from a eutectic mixture of sodium and potassium. The mixture generally contains from about 50–95% by weight potassium by weight, typically 60 to 90% by weight and most preferably from 70 to 80% by weight potassium. The concentration of the eutectic sodium potassium mixture is not critical although concentrations of sodium potassium mixture above the solubility limit of the resulting amides offers no advantage. Generally, the eutectic mixture ranges from about 0.01 to about 0.70 percent by weight, typically from about 0.10 to about 0.60 percent and most preferably from about 0.25 to about 0.55 percent by weight based on the weight of vinylcyclohexane in the system. Eutectic sodium potassium mixtures are commercially available from Calley Chemical Company, Pittsburgh, Pa.

An initiator is also provided to the vinylcyclohexene, ammonia and alkali metal reactants. Illustrative initiators include ferrocene, carbon steel, Fe$_2$O$_3$, FeCl$_3$, Fe(NO$_3$)$_3$ as well as other transitional metal salts and oxides, of which ferrocene is preferred. The amount of initiator employed is not critical and generally very small levels are required. Typically, the level of initiator employed is approximately from about 2 to about 30 and preferably from about 4 to about 10 percent by weight of the amount of alkali metal employed.

The reaction pressure within the reactor must be maintained so as to ensure that the ammonia remains in the liquid phase. Liquid ammonia is necessary to ensure adequate contact between the alkali metal and the ammonia. Accordingly, the reaction pressure must exceed the vapor pressure of ammonia at the reaction temperature. Reaction pressure may vary widely from about 15 pounds per square inch absolute (which is slightly above the vapor pressure of ammonia at 25° C.) to about 1000 pounds per square inch.

The reaction temperature may vary widely from about 25° to about 400° C., generally from about 50° to about 300° C. and preferably from about 75° to about 150° C. Higher temperatures are believed to be advantageous in performing the reaction, however, the preferred temperatures are employed because of safety concerns involving control of the reaction and possible overpressuring of the reactor.

The method in which the alkali metal and initiator are provided to the reactor is not critical. Preferably, a batch reactor is preferred although continuous plug flow and stirred tank reactors may also be employed. Those with skill in the art will readily appreciate that the present invention can be conducted in continuous, batch and semi-batch methods.

The present invention advantageously employs a catalyst system, alkali metal in ammonia, to form a homogeneous system that does not require a separate catalyst preparation step since the catalyst is formed in the reactor. Therefore, the present invention does not require the use of a second reagent which are required in hydrogen transfer reactions disclosed in the prior art.

Through the method of the present invention, ethylbenzene is produced in high yields, greater than 95% by weight and typically greater than 98% by weight. These high yields are obtained without the use of expensive metals or separate catalyst preparation systems, as disclosed in the prior art, e.g., U.S. Pat. No. 4,375,571.

Another advantage of the present invention is that any isomer of vinylcyclohexene is converted to ethylbenzene. Contrary to the disclosure of the prior art, the various isomers are all converted to ethylbenzene. The present invention does not require the isolation of a specific isomer as a reactant before the reaction to ethylbenzene is carried out. This results in a significant cost savings in the cost of the raw material and also results in the higher conversion rate of ethylbenzene since all of the isomers are converted to ethylbenzene rather than various byproducts.

The method of the invention is illustrated by the following Examples. These Examples are set forth for illustration only and are not to be construed as limitations on the present invention except as set forth in the appended claims. All parts and percentages are by weight unless otherwise specified.

Equipment Description

The experimental equipment in which the Examples were conducted consisted of a 300 milliliter stirred stainless steel pressure reactor. The reactor was heated by an external electric heating source (1.2 Kilowatts). Reaction pressure was maintained constant through the use of an internal cooling coil. A solenoid valve was actuated when reaction temperature exceeded the temperature setpoint which allowed cooling water to enter the coil. When reaction temperature was reached the solenoid valve closed thereby shutting off the cooling water to the coil. A dip tube was attached to the reactor so that catalyst could be provided to the reactor.

EXAMPLE 1

Sodium potassium mixture (0.86 grams) was added to a solution containing 38 grams of ammonia, 113 grams of vinyl cyclohexene and 86 milligrams of ferrocene. Reaction temperature (110° C.) and pressure (900 psig) were maintained for 40 minutes.

Gas chromatography analysis of the resulting product revealed 98.9 percent ethylbenzene and no unreacted vinylcyclohexene.

EXAMPLE 2

The conditions and reactant amounts of Example 1 were repeated except that 0.42 grams of the sodium potassium eutectic mixture was employed. After a 40 minute reaction, conducted at 110° C. and 900 psig gas, chromatography on the resulting product revealed 98.9 percent by weight ethylbenzene and no detectable levels of vinylcyclohexene.

EXAMPLE 3

Sodium potassium catalyst (0.42 grams) was added to a solution containing 25 grams of ammonia, 138 grams of vinylcyclohexene and 46 milligrams of ferrocene. After a 40 minute reaction at 110° C. and 900 psig, gas chromatography results indicated that the resulting product contained 89.6 percent ethylbenzene and no detectable levels of vinylcyclohexene.

EXAMPLE 4

Sodium potassium catalyst (0.69 grams) was added to a solution containing 83 grams of vinylcyclohexene, 56 grams of ammonia and 45 milligrams of ferrocene. After a 20 minute reaction conducted at 110° C., 900 psig, the resulting product was found to contain 98.6 ethylbenzene and no detectable levels of vinylcyclohexene.

EXAMPLE 5

Sodium potassium catalyst (0.82 grams) was added to a solution containing 37 grams of ammonia, 111 grams of vinylcyclohexene and 46 milligrams of ferrocene. The contents of the reactor were allowed to react for 5 hours at 34° C. and 900 psig. Analysis of the resulting product revealed 91.9 percent ethylbenzene and 2.2 percent vinylcyclohexene.

I claim:

1. A process for converting vinylcyclohexane to ethylbenzene which comprises contacting the vinylcyclohexane with at least about 15 weight percent ammonia, based on the weight of vinylcyclohexane and ammonia, in the presence of an alkali metal and an initiator selected from the group consisting of ferrocene, carbon steel, $Fe_2O_3$, $FeCl_3$ and $Fe(NO_3)_3$ at a temperature of from about 25 to about 400° C. and a pressure of about 15 to about 1000 pounds per square inch absolute.

2. The process of claim 1 wherein the yield of ethylbenzene is in excess of about 95 percent by weight.

3. The process of claim 1 wherein the contacting is conducted in the presence of a mixture of sodium and potassium.

4. The process of claim 3 wherein the mixture comprises from about 50 to 95 weight percent potassium.

5. The process of claim 4 wherein the mixture is present in an amount of from about 0.01 to 0.70 weight percent based on the weight of vinylcyclohexane.

6. The process of claim 1 wherein the initiator is present in an amount of from about 2 to about 30 weight percent of the amount of the alkali metal.

7. In a process for converting vinylcyclohexane to ethylbenzene by the dehydrogenation of the vinylcyclohexane in the presence of an alkali metal; the improvement which comprises contacting the vinylcyclohexane with the alkali metal in the presence of at least about 15 weight percent ammonia based on the weight of vinylcyclohexane and ammonia.

8. The process of claim 7 wherein the concentration of ammonia is from about 15 to about 40 weight percent based on the weight of vinylcyclohexane and ammonia.

9. The process of claim 8 wherein the concentration of ammonia is from about 25 to 40 weight percent based on the weight of vinylcyclohexane and ammonia.

10. The process of claim 7 wherein the contacting is conducted in the presence of an initiator selected from the group consisting of ferrocene, carbon steel, $Fe_2O_3$, $FeCl_3$ and $Fe(NO_3)_3$.

* * * * *

UNITED STATES PATENT AND TRADEMARK OFFICE
CERTIFICATE OF CORRECTION

PATENT NO. : 5,321,180
DATED : June 14, 1994
INVENTOR(S) : Clark S. Davis

It is certified that error appears in the above-identified patent and that said Letters Patent is hereby corrected as shown below:

For "vinylcyclohexane" read "vinylcyclohexene" at each occurrence in column 4, lines 24, 25-26, 27, 42, 46, 47-48, 49-50, 52, 55 and 58.

Signed and Sealed this

Second Day of May, 1995

BRUCE LEHMAN

Attest:

Attesting Officer

Commissioner of Patents and Trademarks